(12) United States Patent
Carney et al.

(10) Patent No.: US 7,684,872 B2
(45) Date of Patent: Mar. 23, 2010

(54) CONTACTLESS INTERCONNECT FOR TRANSDUCERS

(75) Inventors: James K. Carney, Brooklyn Park, MN (US); Michael A. Schugt, Saint Paul, MN (US); Qingshan Ye, Plymouth, MN (US); Can Cinbis, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 806 days.

(21) Appl. No.: 11/380,315

(22) Filed: Apr. 26, 2006

(65) Prior Publication Data

US 2007/0255166 A1 Nov. 1, 2007

(51) Int. Cl.
*A61N 1/08* (2006.01)
(52) U.S. Cl. .......................... 607/116; 607/37
(58) Field of Classification Search ................. 600/486; 607/2, 9, 17, 21, 116, 119
See application file for complete search history.

(56) References Cited

U.S. PATENT DOCUMENTS

| | | | |
|---|---|---|---|
| 3,503,034 A | | 3/1970 | Appleton |
| 4,770,641 A | | 9/1988 | Rowlette |
| 5,458,630 A | * | 10/1995 | Hoegnelid et al. .......... 607/116 |
| 6,198,952 B1 | | 3/2001 | Miesel |
| 6,221,024 B1 | * | 4/2001 | Miesel ....................... 600/486 |
| 6,529,778 B2 | | 3/2003 | Prutchi |
| 6,591,143 B1 | * | 7/2003 | Ekwall ....................... 607/116 |
| 6,725,092 B2 | * | 4/2004 | MacDonald et al. ........... 607/2 |
| 7,065,411 B2 | * | 6/2006 | Verness ....................... 607/116 |
| 2002/0156417 A1 | | 10/2002 | Rich et al. |
| 2003/0109901 A1 | * | 6/2003 | Greatbatch .................... 607/9 |
| 2003/0125774 A1 | * | 7/2003 | Salo ............................ 607/21 |
| 2004/0193021 A1 | | 9/2004 | Zdeblick et al. |
| 2004/0215300 A1 | * | 10/2004 | Verness ....................... 607/116 |
| 2006/0283007 A1 | | 12/2006 | Cros et al. |

FOREIGN PATENT DOCUMENTS

| | | |
|---|---|---|
| EP | 074114 A | 3/1983 |
| WO | WO/2004052182 A | 6/2004 |
| WO | WO/2006029090 A | 3/2006 |

OTHER PUBLICATIONS

Liu, Chun-Hung; Wade, Eric; and Asada, Harry. Reduced-Cable Smart Motors Using DC Power Line Communications. Proceedings of the 2001 IEEE International Conference on Robotics and Automation. May 21-26, 2001.*
International Search Report, PCTUS/2007/066585, Oct. 24, 2007, 6 Pages.

* cited by examiner

*Primary Examiner*—Carl H Layno
*Assistant Examiner*—Luther G Behringer
(74) *Attorney, Agent, or Firm*—Stephen W. Bauer; Michael C. Soldner (57) ABSTRACT

A medical device for implantation within a patient comprising a lead body including a conductor within the lead body and a transducer supported by the lead body. The conductor is electrically coupled to the transducer by a conductive fluid, paste or gel. The conductive fluid, paste or gel may be contained within a well in the lead body. The transducer may be a MEMS chip and/or an integrated circuit and may perform any of a variety of functions such as sensing physiological data.

24 Claims, 7 Drawing Sheets

CONTACTLESS INTERCONNECT FOR TRANSDUCERS

BACKGROUND

Implantable medical devices (IMDS) are commonly employed in medical therapies such as cardiac rhythm management (CRM), neurological monitoring and therapy, and other diagnostics and monitoring. Such CRM devices may be coupled to a surface of a patient's heart via one or more medical electrical leads. Typically the one or more leads include electrodes for both stimulating the heart and sensing electrical activity of the heart. In order to provide better management of cardiac conditions, one or more leads may also include a physiological sensor such as a transducer. In addition to intracardiac leads, transducers may also be incorporated into leads that are placed in the abdomen, subcutaneously or submuscularly in the thorax or in or around the cranium to measure specific physiologic variables. In many cases, it is desirable that all of the necessary elements, including electrodes and/or transducers, be carried on a single lead body wherein locations of each element along the lead body accommodate proper function to meet the therapeutic objective of the system. Because it is desirable to maintain a small lead diameter while including multiple lead components, it may be preferable that the size of the transducer be as small as possible.

In addition to having a small size, transducers contained within leads must be designed to function well in the environment in which they will be placed. For example, transducers that are exposed to a patient's body are susceptible to corrosion such that integrated circuit chips included in the transducers may degrade over time. To prevent exposure to bodily fluids, transducers may be enclosed in hermetically sealed capsules. The transducer, inside the capsule, is electrically joined to a power source through an electrical feedthrough which may rigidly attach the transducer to the lead. By isolating the transducer, this configuration decreases corrosion, allowing for long-term implantation. However, when the transducers are disposed in or near a patient's heart, heart contractions may cause force to be repeatedly applied to the rigid connection between the transducer and the lead. This undesirable strain may decrease the structural integrity of the transducer over time. Transducers on leads that are placed subcutaneously or intramuscularly would also be subjected to repeated strain due to patient movements. In addition, encasing the transducers in hermetically sealed capsules has the undesirable effect of increasing their size. Some transducers, such as biochemical sensors, cannot be encased in hermetic capsules because they need to interact with the body fluids.

Accordingly, it is desirable to have a relatively simple and inexpensive transducer that has a corrosion resistant configuration and is capable of being implanted into a patient for long periods of time. In addition, it is desirable that the transducer be small to fit within the circumference of an implanted medical device, such as an intracardiac lead. In addition, it is desirable to have a transducer that is configured to be tolerant to strain, such as due to repetitive lead movement caused by cardiac activity.

SUMMARY

Embodiments of the invention include implantable medical devices including, for example, pacemakers, cardiac resynchronization devices, implantable defibrillators and physiologic monitors. The implantable medical devices may comprise lead bodies including one or more conductors within the leads and one or more transducers supported by the lead by for detecting physiological data. The one or more transducers are electrically coupled to the one or more conductors by a conductive fluid, paste or gel. In some embodiments, the transducer may be media exposed. The conductive fluid, paste, or gel that couples the transducer to the conductor may be contained within a well in the lead body. Embodiments of the invention include leads such as intracardiac leads, intravascular leads, subcutaneous leads and submuscular leads.

A variety of transducers are appropriate for embodiments of the invention. In some embodiments, the transducer may be a MEMS chip and/or an integrated circuit. The transducer may perform a variety of functions. For example, the transducer may be a sensor such as a pressure sensor, an accelerometer, an acoustic sensor, a flow sensor, a glucose sensor, a biochemical sensor, a pH sensor, and/or a strain gauge. The conductor may provide power to one or more transducers as well as other lead body components and/or may provide data transmission.

DETAILED DESCRIPTION

Figure 1:
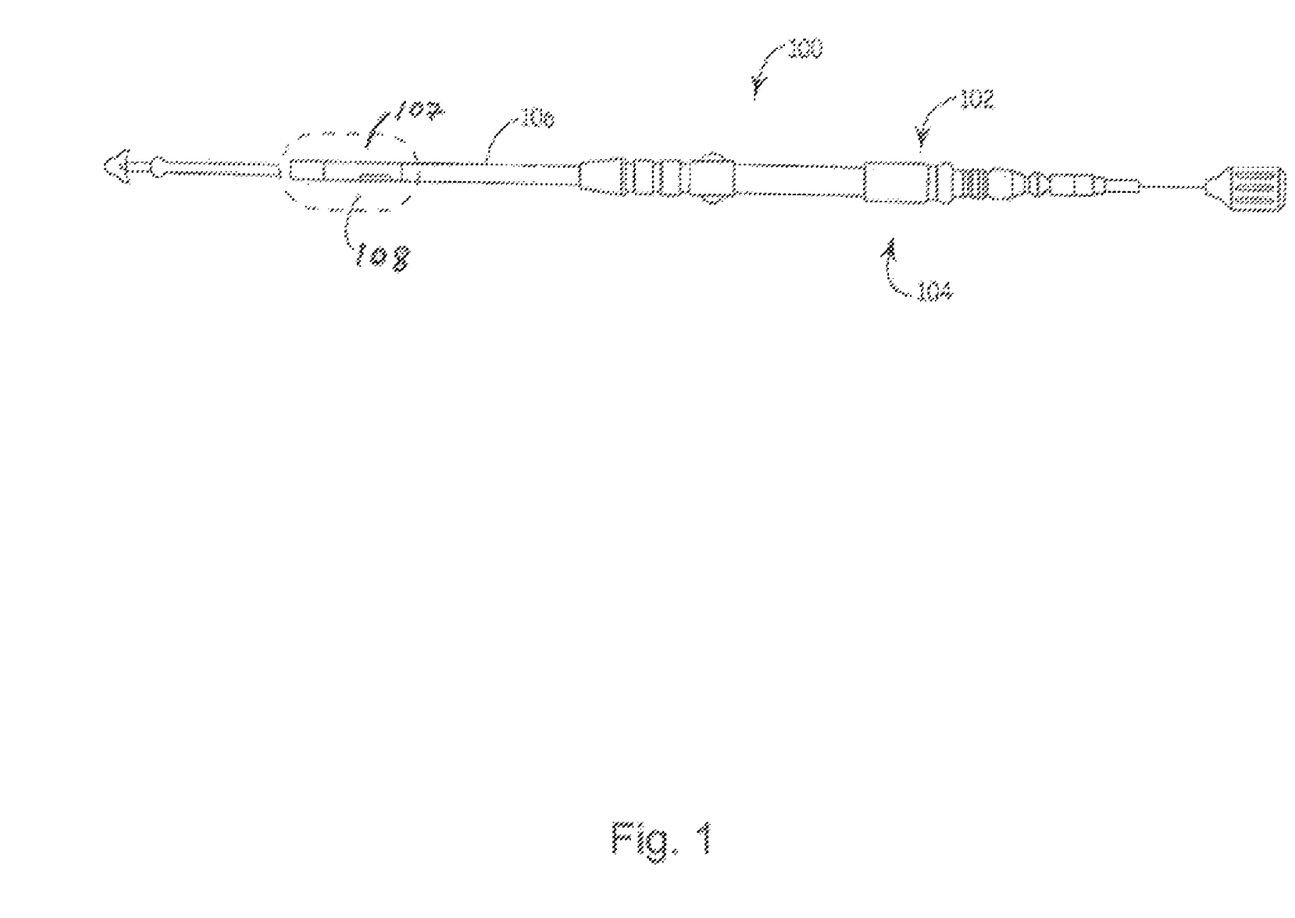
FIG. 1 is a side view of an exemplary lead.

Embodiments of the invention may be used in implantable medical devices having conductive bodies such as lead bodies. An example of an implantable medical device appropriate for the invention is an implantable medical electrical lead such as an intracardiac medical lead 100. FIG. 1 is a side view of an exemplary intracardiac medical lead 100 configured to be coupled to an implantable medical device or other monitoring device (not shown) and includes a transducer 108. Lead 100 may be any one of a number of different types of leads, such as a pressure monitoring lead or a therapy lead. Lead 100 includes a connector assembly 102, a lead body 106, and a transducer module 107. Connector assembly 102 is located at a proximal section 104 of lead 100 and may be configured to be coupled to an implantable medical device (not shown) to electrically couple lead 102 thereto. Other examples of transducers on conductive bodies include conductive bodies that connect an implanted medical device to transducers placed in the abdomen or subcutaneously or submuscularly in the thorax or EEG electrodes on or around the cranium. Examples of appropriate implantable medical devices for use in this invention include pacemakers, defibrillators, cardiac resynchronization therapy (CRT) systems, cardiac or pulmonary monitors, glucose and other chemical monitors, neurostimulators, neurological monitors, neuromuscular sensors and actuators, and drug pumps.

The transducer module 107 may support any type of transducer 108 suitable for incorporation within a conductive body. For example, the transducer 108 may be a sensing transducer, an actuating transducer, an IC only transducer, or a combination of a sensor and an actuator. Examples of sensing transducers include a sensor and an integrated circuit integrated on a chip (e.g., a silicon substrate or micro-electromechanical system (MEMS) device or nano-electro-mechanical system (NEMS) device), a sensor element without an integrated circuit built into a substrate (e.g., glass, ceramic, silicon, or other suitable material), and a sensor element built into a substrate with an integrated circuit hermetically encapsulated or packaged into a substrate. Sensors which may be used to detect physiologic data include pressure sensors, oxygen sensors, flow sensors, temperature sensors, accelerometers, acoustic sensors, biochemical sensors, optical sensors and sensors which monitor more than one physiological variable. Examples of actuating transducers include an actuator and an integrated circuit integrated on a chip (e.g., a silicon substrate or MEMS device or NEMS device), an actuator element without an integrated circuit built into a substrate (e.g., glass, ceramic, silicon, or other suitable material), and an actuator element built into a substrate with an integrated circuit hermetically encapsulated or packaged into a substrate. Such actuating transducers may include a piezoelectric element actuator for vibration. Examples of IC-only transducers include an integrated circuit on a silicon substrate (e.g., an IC-logic multiplexer on a lead or a memory chip for sensor calibration coefficients) and an integrated circuit hermetically encapsulated or packaged into a substrate (e.g., glass, ceramic, silicon, or other suitable material). Alternatively, embodiments of this invention may include components instead of, or in addition to, transducers 108. Examples of other components which may be used in embodiments of this invention include transceivers, pumps, drug delivery devices, thermocouples and other small devices suitable for inclusion in a conductive body.

The transducer 108 may be located within a conductive body such as a lead body 106 and does not need to be encased in a hermetically sealed capsule. Rather the transducer 108 may be surrounded by a sheath 110, a capsule or other appropriate material or may be made from biocompatible material. In some embodiments, at least a portion of the transducer 108 may be media exposed for interacting with the implant environment and sensing one or more physiological variables. Transducers that may require exposure to the physiologic media include, but are not limited to, pressure sensors, flow sensors, glucose sensors, pH sensors and other chemical sensors. Other transducers that may not require exposure to the physiologic media include, but are not limited to, accelerometers, temperature sensors, and acoustic sensors. These transducers would be made smaller with the elimination of the hermetic capsule.

As shown in FIGS. 2-7, the conductive body such as a lead body may include an outer sheath 110 and a backbone 112. The outer sheath 110 and the backbone 112 of the conductive body may surround a portion of the transducer 108. The outer sheath 110 and the backbone 112 may be made of a nonconductive material such as polymer, glass, ceramic or an inorganic metal oxide. The appropriate material for the sheath 110 and/or backbone 112 may be chosen to provide the desired stiffness or flexibility of the conductive body.

In some embodiments, the transducer 108 is a pressure sensor 114. In such embodiments, the pressure sensor 114 may be configured to sense pressure exerted upon it by a patient's blood or other body fluid. The pressure sensor 114 may include a pressure transducer. The transducer may include a MEMS/IC or a NEMS/IC on a substrate. In some embodiments, a complementary metal oxide semiconductor (CMOS) buffer amplifier may be used in place of, or in addition to, the MEMS/IC or NEMS/IC. The MEMS/IC or NEMS/IC may be configured to convert sensed pressure into representative signals. The transducer may include a flexible diaphragm 120 that, when subjected to fluid pressure, may create a capacitance with a nearby fixed plate. In some embodiments, the transducer may include piezoelectric material that creates an electrical signal when subjected to a force due to surrounding fluid pressure. The pressure transducer may also include at least one conductive pad 116, which provides an electrical connection to other components. Other types of transducers may also have at least one conductive pad 116.

The transducer 108 may be supplied with power by conductors 118 that pass through the conductive body to the transducer 108. These conductors 118 may be surrounded by the backbone 112 as they pass through the conductive body. In addition, the conductors 118 may be surrounded by insulation. These conductors 118 may be wire coils, such as single pole coiled wire conductors, and may be made of a suitable biocompatible material such as MP35N. In some embodiments, such as MEMS pressure sensors, the conductors provide low voltage power, on the order of microamperes, to the transducers 108. The conductors 118 may also transmit data to a device, such as a monitoring device, from the sensors 108. In some embodiments, the conductors 118 may be bi-directional and may supply power to the transducer 108 as well as transmit data from the transducers 108 to the monitoring device.

When the conductor 118 reaches the transducer 108, there is a gap in a portion of the backbone 112 such that the backbone 112 no longer surrounds the conductor 118. This gap is located along a length of conductor 118 which extends adjacent to a conductive pad 116 of the transducer 108. The gap extends at least from the conductor 118 to the conductive pad 116, creating a well 122 which encompasses both components. A portion or all of the conductor 118 is without insulation within the well 122.

In some embodiments, the well 122 is completely surrounded by insulating material. The well may extend through the backbone 112 from the conductive pad 116 to the sheath 110, or may only extend through a portion of the backbone 112. In some embodiments the conductive body may have a backbone 112 but no separate sheath 110. In such embodiments, the well 122 may not extend through to the outer circumference of the backbone 112, but rather the backbone 112 may enclose the well 122. Alternatively, the well 122 may extend through the backbone 112 and a nonconductive material may cover the well 122. In such embodiments the well 122 is an opening within the conductive body which contains a conductive pad 116 and a conductor 118 and which is electrically isolated.

Inside the well 122, there is no hard wire or other structural connection between the conductor 118 and the conductive pad 116. Rather, the well contains an electrically conductive material which electrically connects the conductor 118 and the conductive pad 116. For example, in one embodiment, the well 122 may be filled with an ionic conductive fluid or gel. Examples of appropriate conductive fluids or gels include physiologic saline, ionic liquid, inorganic salt solution in a hydrogel, organic salt solution in oil or hydrophilic liquid-like polymers. In another embodiment, the well 122 may be filled with an electrically conductive paste, polymer gel or adhesive. Examples include pastes containing carbon-graphite or silver powder, conductive gaskets, conductive polymers such as polypyrrole, polyacetylene and polyaniline, conductive carbon or metal nanoparticle filled oil or polymer with a glass transition temperature lower than room temperature, and liquid metals.

Eliminating the hard conductor interconnection between the transducer and the conductors allows the conductive pad 116 and the conductor 118 to move relative to each other without interfering with their electrical connection. Such a flexible system is ideal for an environment in which the transducer 108 will undergo repeated stresses over a long period of time, such as a permanent intracardiac lead. As a result of this improved flexibility, the system may have less stress or strain induced failures relative to systems with rigid interconnections, making the connection more reliable. At the same time, elimination of the feedthrough has the additional advantage of making the system smaller. This allows the lead 100 or other conductive body to be small and isodiametric.

The conductor 118 which supplies power to the transducer 108 may terminate inside the well 122. Alternatively, the conductor 118 may pass through the well 122 and reenter the backbone 112. The conductor 118 may then continue distally through the conductive body and supply power to and/or receive data from other conductive body components such as one or more additional transducers 108, pumps, pacing tips, defibrillation coils, or other devices. In this way a single conductor 118 is able to supply power to and/or receive data from multiple transducers 108 or a combination of components.

Figure 2:
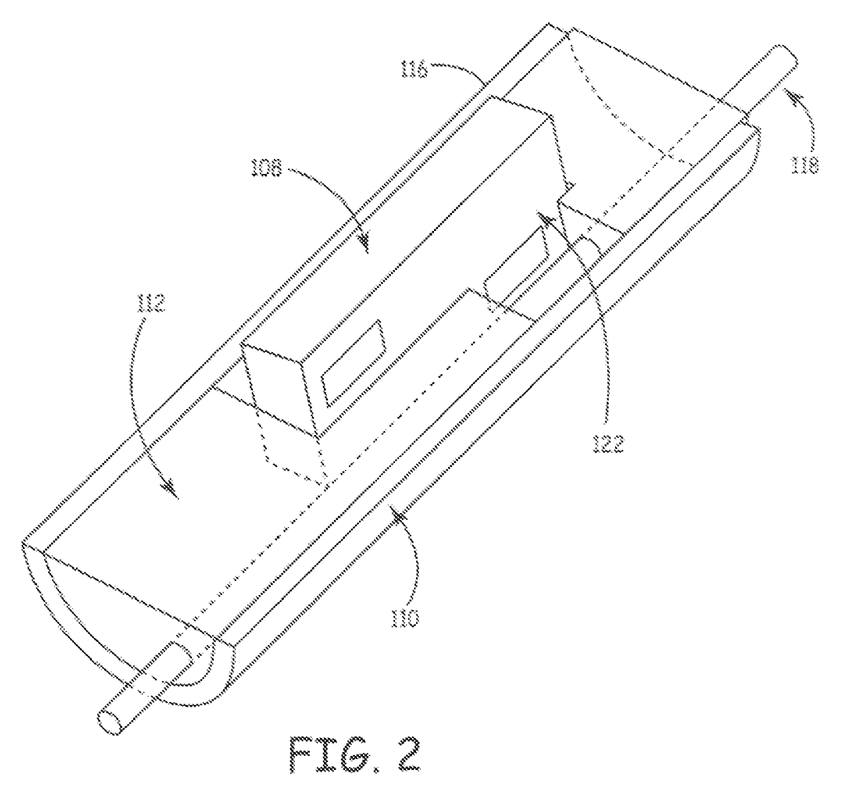
FIG. 2 is a partial cross section of a portion of a lead according to an embodiment.

In some embodiments, the transducer 108 has two conductive pads 116, each on the same side of the transducer as shown in FIG. 2. Half of the backbone 112 has been cut away in this view to reveal the well 122 surrounding the lower conductor 118 and conductive pad 116. The conductor 118 which is electrically connected to the upper conductive pad 116 is not shown. The conductive pads 116 on the transducer 108 are spaced such that the wells 122 in which they are contained are separated by the backbone 112 and the wells 122 are electrically isolated from each other. Alternatively, a different insulative material other than the backbone 112 could separate and electrically isolate the wells 122.

Figure 3:
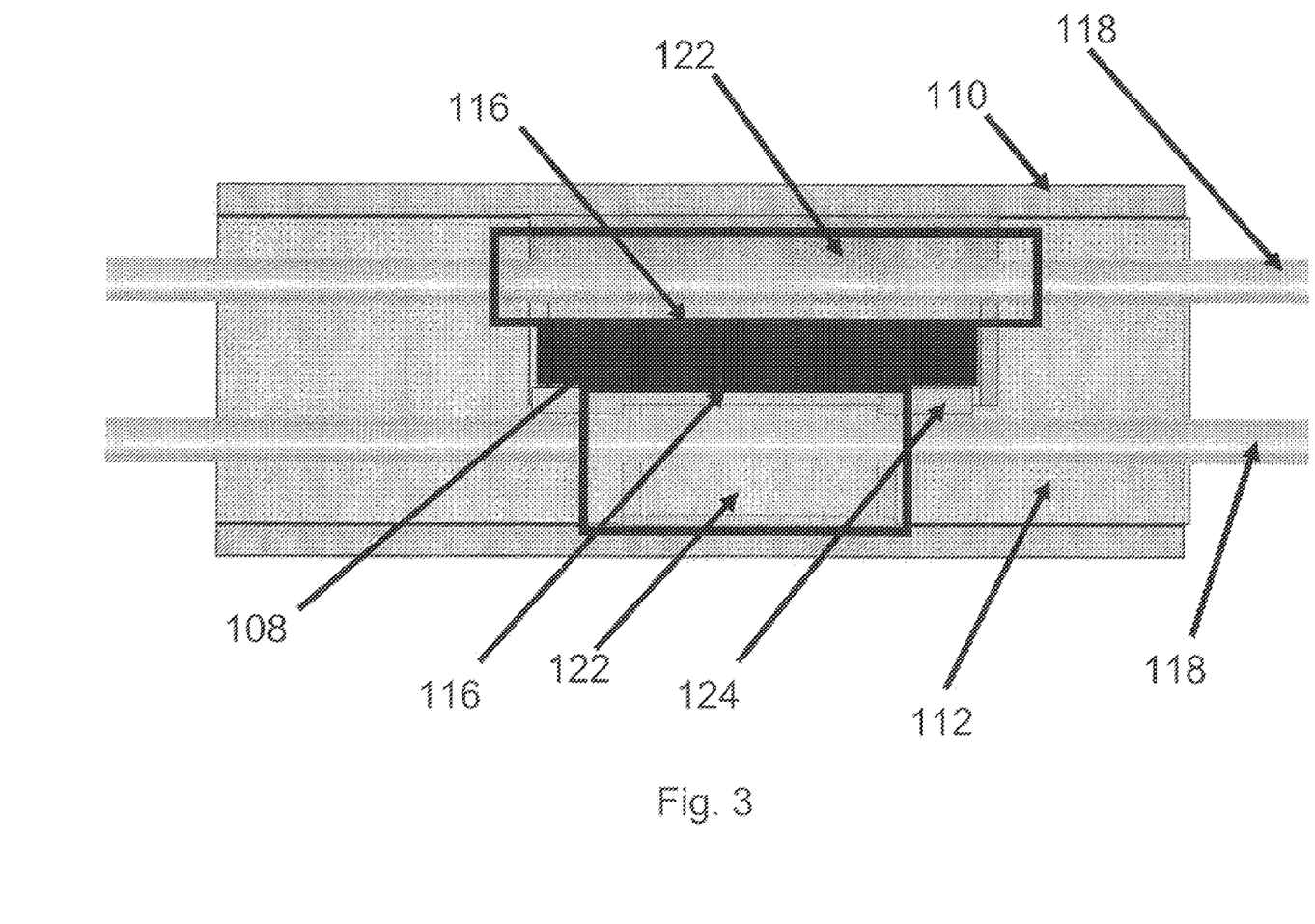
FIG. 3 is a cross section of a portion of a lead according to another embodiment.
Figure 4:
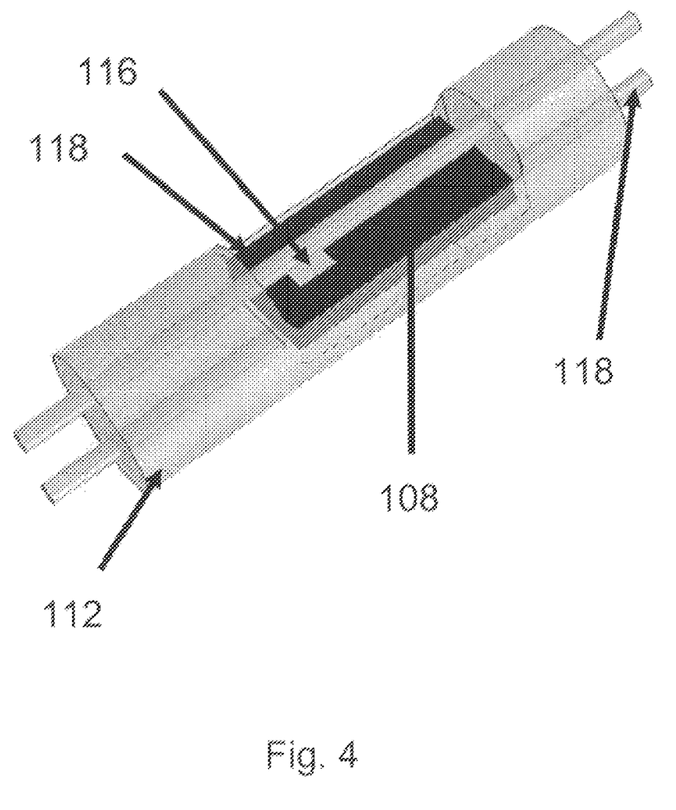
FIG. 4 is a portion of a lead with a section of the sheath and backbone cut away.

In other embodiments, the transducer 108 has conductive pads 116 on opposite sides of the transducer 108, as shown in FIGS. 3-4. FIG. 3 is a cross section of a segment of a conductive body in which one well 122 encloses a conductor 118 and conductive pad 116 above the transducer 108 and another well 122 encloses the other conductor 118 and other conductive pad 116 below the transducer 108. The conductors 118 pass through the wells 122 and continue through the conductive body. A seal 124, such as an adhesive or silicone, may be provided around the well 122, as shown in FIG. 3. The wells 122 are electrically isolated from each other. In FIG. 4, the portion of the sheath 110 and backbone 112 above the transducer 108 are cut away to show the conductor 118 passing above the conductive pad 116.

Figure 5:
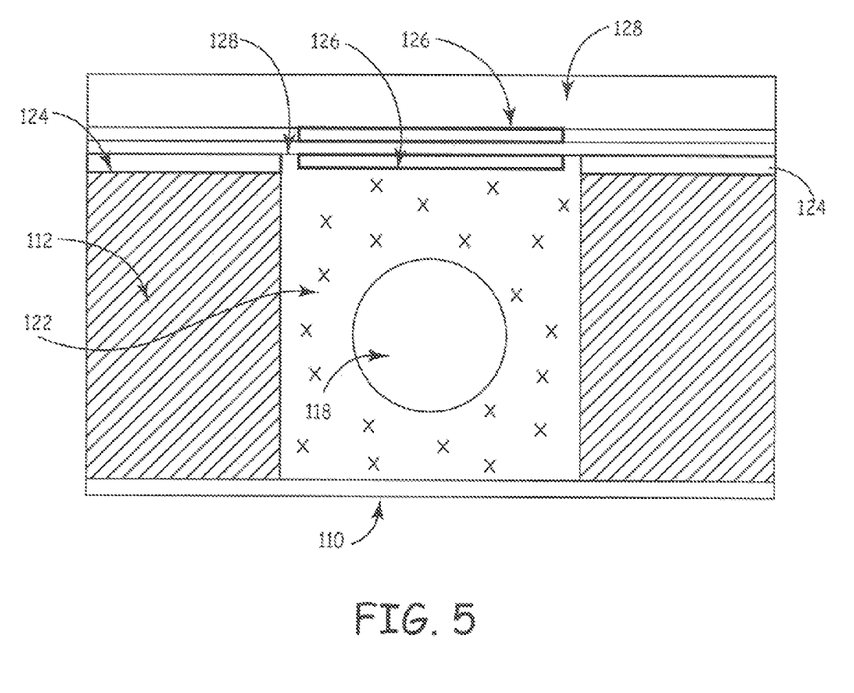
FIG. 5 is a cross section of a transducer and conductive body in a well including a capacitor plate.

In some embodiments, such as the one shown in FIG. 5, the conductive fluid or gel is capacitively coupled to the conductive pad. In the embodiment shown in FIG. 5, upper and lower capacitor plates 126 separated by a dielectric layer 128 form a capacitor. The upper capacitor plate 126 (as shown in FIG. 5) forms an inner plate while the lower capacitor plate 126 is positioned within the well 122 and acts as the conductive pad 116. Capacitive couplings, such as that shown in FIG. 5, allow the entire pressure module and/or ICs that are susceptible to corrosion from body fluids to be coated in the dielectric 128 to help isolate the module from the surrounding media yet provide electrical coupling via a fluid gel in well 122 to conductor 118. That is, the dielectric 128 in FIG. 5 may be applied over upper plate 126 for capacitive purposes and over the remainder of the module for media isolations purposes. Appropriate transducers for use in these embodiments include silicon MEMS pressure sensors and accelerometers.

The dielectric 128 may be formed by atomic layer deposition or other coating processes. Other transducers, such as optical based or electrochemical sensors, may be coated with a thin layer of silicone or other polymer. Additionally, the capacitor may act with an adhesive layer seal 124 to seal off well 122. In an alternative embodiment, the upper capacitive plate may be coated with a dielectric without a lower capacitive plate such that the capacitor is formed by the upper capacitive plate and the conductive media.

In some capacitive embodiments, enhancements can be made to the capacitor plates to increase the capacitance and, thereby, lower the impedance of the connection. For example, by increasing the surface area of the plates 126, the capacitance may be increased. This may be done, for example, by making the surface of one or both of plates 126 irregular, such as by using jagged or undulated surface. In this way the active surface area of the plates 126 may be increased without increasing the size of the plates 126, thus maintaining the desired small size of the connection. Such surfaces may be created using materials such as titanium nitrate, which may be applied using a sputtering process, or plantinum black, which may be applied by an electroplating or electrodeposition process. In some embodiments, such as embodiments having a single capacitive plate, porous silicone with a high dielectric constant may be used as a film to increase the surface area and capacitance of the plate. This embodiment may be appropriate, for example, when the transducer and electronics are a single piece of silicon. The back side of the silicon chip may be processed to make it porous such that it may be coated with a suitable insulating film.

In addition, it may be desirable to minimize the distance between the conductive pad 116 and the conductor 118, thus minimizing the resistance as well as providing a small size. While the conductive pad 116 and the conductor 118 may be so close that they touch, physical contact is not necessary using the conductive fluid or gel according to embodiments of the invention. Thus, by eliminating a hard physical connection, the design accommodates flexion and movement of the conductive pad 116 relative to the conductor 118 while maintaining an electrical connection.

Figure 6:
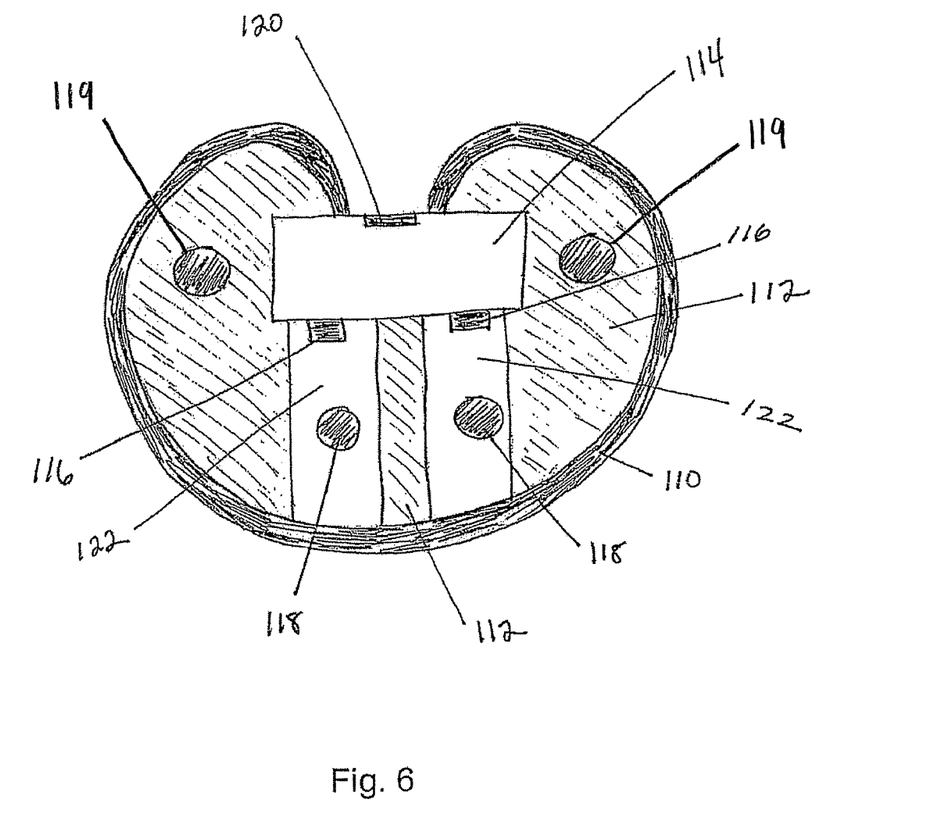
FIG. 6 is a cross section of a pressure sensor within a lead.
Figure 7:
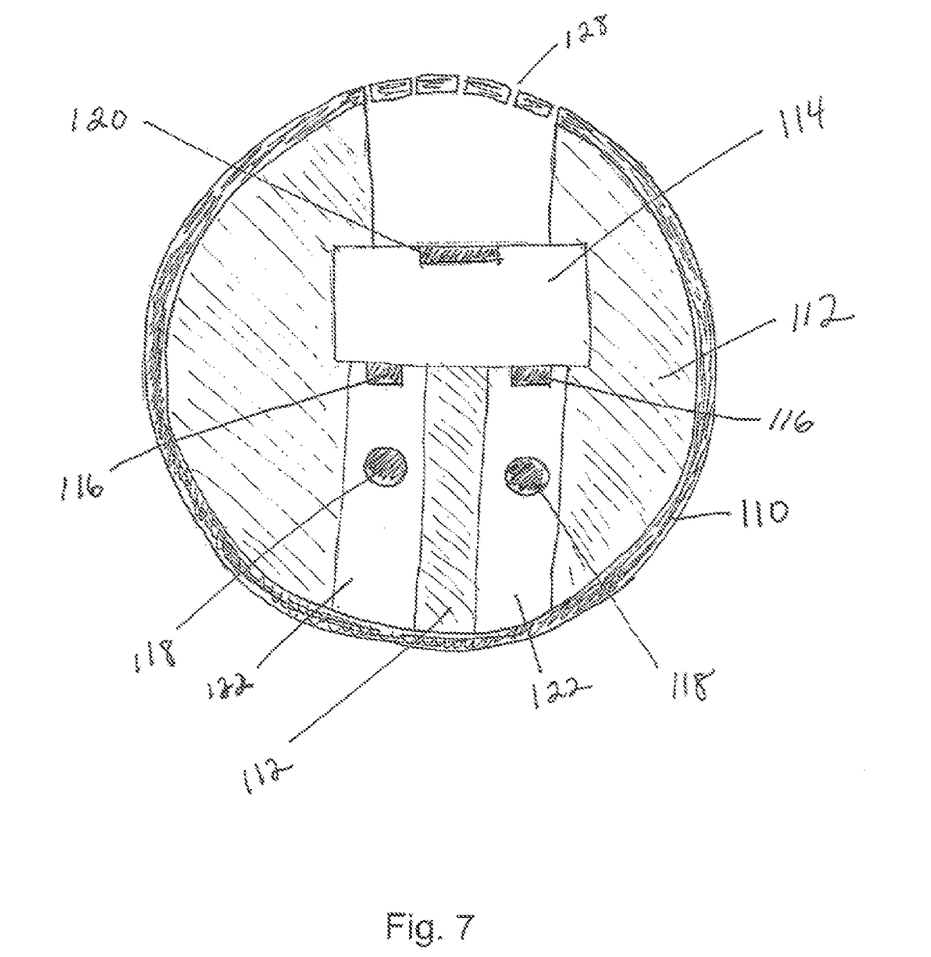
FIG. 7 is a cross section of a pressure sensor within a lead according to another embodiment.

At least a portion of the transducer 108 may be media exposed to allow communication with the environment. The conductive body which contains the transducer 108 may include an opening over a portion of the transducer. In some embodiments, the transducer 108 may be a pressure sensor 114 for detecting pressure, such as the pressure exerted upon the pressure sensor 114 by a patient's blood flowing around the pressure sensor 114. Such pressure sensors 114 may have diaphragms 120 or membranes on their surface, which may be exposed to the environment. In embodiments which include a pressure sensor 114 within a lead 100 or other conductive body, the diaphragm 120 of the pressure sensor 114 may be media exposed through an opening in the sheath 110. For example, as shown in FIG. 6, the sheath 110 may form an opening by being completely absent over the exposed portion of the pressure sensor 114, in this case over a diaphragm 120. The exposed portion of the transducer 108 may be partially sheltered by being located somewhat centrally within the circumference of the lead, such as inside an indentation in the sheath 110 and backbone 112 as shown in FIG. 6. Alternatively, as shown in FIG. 7, the sheath 110 may form an opening by having one or more small holes or pores 128 over the exposed portion of the transducer 108. The use of pores 128 may shelter the exposed portion of the transducer 108. It may also allow for selective filtration of the bodily fluids to which the transducer 108 is exposed. For example, for conductive bodies placed in the circulatory system, the pores 128 may filter the blood cellular components such that the transducer 108 is only exposed to plasma. Alternatively, such as in the case of biochemical sensors, the pores 128 may be a semi-permeable membrane that allow entry of the substance of interest, such as a chemical, but minimize or exclude diffusion of other substances which may be sources or error. Such arrangements may prevent encapsulation and/or minimize the formation of fibrotic tissue. Prevention of cell adhesion directly on the sensing material may reduce or prevent biocorrosion and/or biofouling. It may also improve transducer performance by reducing sensor drift.

In another embodiment, the transducer 108 may not be media exposed. For example, the transducer 108 may be a pressure sensor 114 including a diaphragm 120. The diaphragm 120 may be contained within a well 122 in the backbone 112 which also contains the conductor 118 and the conductive pad 116. Thus the diaphragm 120 may be contained within the well 122 and surrounded by a conductive fluid or gel. The well 122 may be encased by the sheath 110 which may be sufficiently flexible to allow transmission of pressure through the fluid or gel of the well 122 to the diaphragm 120. Alternatively, a flexible capsule may surround the well 122 in addition to or instead of the sheath 110. Thus the same fluid or gel that provides conduction between the pad 116 and the conductor 118 may also transmit pressure to the sensor diaphragm 120.

In some embodiments, the conductive body such as a lead body may include one or more optional conductors 119, in addition to the conductors 118 which supply power to and/or transmit data from the transducer 108. These conductors 119 pass through the back bone 112 but do not enter the wells 122. The cross section of a conductive body shown in FIG. 6 contains conductors 118 which supply power to a transducer 108 within wells 122 as well as two optional conductors 119. In some embodiments, these optional conductors 119 may be at a higher voltage than the conductors 118 which power the transducer 108, making them appropriate for providing power to applications such as electrodes for cardiac pacing.

The invention claimed is:

1. A medical device for implantation within a patient, comprising:
    a lead body comprising a proximal section and at least one solid conductor extending distally within the lead body from the proximal section;
    a transducer supported by the lead body for detecting physiological data, wherein the at least one solid conductor extends distally within the lead body from the proximal section to a location proximate the transducer, and further wherein the transducer is electrically coupled to the at least one solid conductor by a conductive fluid so that the at least one solid conductor provides power to the transducer; and
    a connector assembly supported by the lead body at the proximal section for connection to an implantable medical device.

2. The medical device of claim 1, wherein the conductive fluid comprises at least one of a liquid, a paste, and a gel.

3. The medical device of claim 1, wherein the transducer comprises at least one of a pressure sensor, an accelerometer, an acoustic sensor, a flow sensor, a glucose sensor, a biochemical sensor, a pH sensor, an electrode, and a strain gauge.

4. The medical device of claim 1, wherein the conductive fluid comprises physiologic saline.

5. The medical device of claim 1, wherein the transducer is media exposed.

6. The medical device of claim 1, wherein the implantable medical device comprises at least one of a pacemaker, a cardiac resynchronization device, an implantable defibrillator, and a physiologic monitor.

7. The medical device of claim 1, wherein the transducer comprises at least one of a MEMS chip and an integrated circuit.

8. The medical device of claim 1, wherein the at least one solid conductor further extends distally from the location proximate the transducer to a location proximate another lead body component to provide power to the another lead body component.

9. The medical device of claim 1, wherein the medical device further comprises a well defined adjacent a conductive pad of the transducer, wherein the at least one solid conductor extends distally within the lead body from the proximal section to a location alongside at least a portion of the transducer within the well but spaced apart from the transducer.

10. A lead for an implantable medical device for implantation within a patient comprising:
    a lead body comprising a proximal section and a solid conductor extending distally within the lead body from the proximal section; and
    a transducer supported by the lead body for detecting physiological data, wherein the solid conductor extends distally within the lead body from the proximal section to a location proximate the transducer, and further wherein the transducer is media-exposed when in an implant environment within the patient and is electrically coupled to the solid conductor using a conductive fluid, wherein the conductive fluid comprises at least one of a liquid, a paste, and a gel.

11. The lead of claim 10, further comprising at least one additional solid conductor extending distally within the lead body from the proximal section to a location proximate the transducer without providing power to the transducer.

12. The lead of claim 10, wherein the transducer comprises at least one of a MEMS chip which detects pressure and an integrated circuit which detects pressure.

13. The lead of claim 12, wherein the transducer comprises a diaphragm which is media exposed.

14. The lead of claim 10, wherein the solid conductor also provides data transmission.

15. The lead of claim 10, wherein the transducer is capacitively coupled to the solid conductor.

16. The lead of claim 10, wherein the solid conductor extends distally within the lead body from the proximal section to a location alongside but spaced apart from at least a portion of the transducer.

17. A medical device for implantation within a patient comprising:
    a lead body comprising a proximal section, a supportive backbone, and a well;
    a solid conductor extending distally from the proximal section to the well, wherein the solid conductor is positioned within and passes through the well;
    a transducer for detecting physiological data, wherein the transducer comprises an electrically conductive interface pad located within the well, and further wherein the transducer senses parameter data and provides an electrical signal representative of the sensed parameter data to the interface pad; and
    a conductive fluid filling at least part of the well and electrically coupling the solid conductor and the electrically conductive interface pad.

18. The medical device of claim 17, wherein the lead body further comprises a sheath which surrounds the backbone and retains the conductive fluid within the well, and further wherein the conductive fluid comprises at least one of a liquid, a paste, and a gel.

19. The medical device of claim 17, wherein the surface of the electrically conductive interface pad provides capacitance.

20. The medical device of claim 17, wherein the transducer further comprises an additional electrically conductive interface pad, wherein the lead body comprises an additional well, and wherein the medical device further comprises:
   an additional solid conductor extending distally from the proximal section to the additional well, wherein the additional solid conductor is positioned within and passes through the additional well, wherein the additional electrically conductive interface pad of the transducer is located within the additional well, and wherein a conductive fluid fills at least part of the additional well and electrically couples the additional solid conductor to the additional electrically conductive interface pad.

21. The medical device of claim 20, wherein the well and the additional well are electrically isolated.

22. The medical device of claim 17, wherein the transducer comprises a MEMS chip for detecting pressure.

23. The medical device of claim 17, wherein at least a portion of the well is located alongside at least a portion of the transducer along a length of the lead body.

24. A lead for an implantable medical device for implantation within a patient comprising:
   a lead body comprising a proximal section;
   a transducer supported by the lead body, wherein the transducer is located distally from the proximal section of the lead body, wherein at least a portion of the transducer is media-exposed when in an implant environment within the patient;
   a first solid conductor extending distally within the lead body from the proximal section to a location proximate the transducer, wherein the transducer is electrically coupled to the first solid conductor using a conductive fluid, wherein the conductive fluid comprises at least one of a liquid, a paste, and a gel; and
   a second solid conductor extending distally within the lead body from the proximal section to the transducer, wherein the transducer is electrically coupled to the second solid conductor.

* * * * *